United States Patent [19]

Seidel

[11] 4,017,566

[45] Apr. 12, 1977

[54] VAPORIZER FOR ANAESTHETICS

[75] Inventor: Peter Seidel, Lubeck, Germany

[73] Assignee: Dragerwerk Aktiengesellschaft, Germany

[22] Filed: Feb. 11, 1976

[21] Appl. No.: 657,219

[30] Foreign Application Priority Data

Feb. 20, 1975  Germany .................... 2507281

[52] U.S. Cl. .................. 261/56; 128/187; 128/211; 261/DIG. 65; 261/39 R
[51] Int. Cl.² ..................... A61M 15/00
[58] Field of Search .......... 128/187, 188, 192, 193, 128/211; 261/DIG. 65, 39 R, 56, 63

[56] References Cited

UNITED STATES PATENTS

| | | | |
|---|---|---|---|
| 3,438,372 | 4/1969 | Sugg et al. ................ | 128/188 |
| 3,534,732 | 10/1970 | Bickford .................... | 128/188 |
| 3,651,805 | 3/1972 | Breiling ...................... | 128/188 |
| 3,671,024 | 6/1972 | Breiling ...................... | 128/188 |
| 3,841,560 | 7/1973 | Sielaff ................ | 261/DIG. 65 |

FOREIGN PATENTS OR APPLICATIONS

| | | | |
|---|---|---|---|
| 2,008,359 | 1/1970 | France ...................... | 128/188 |
| 54,378 | 4/1973 | Netherlands ............... | 128/187 |
| 961,503 | 6/1964 | United Kingdom ........ | 128/188 |

*Primary Examiner*—Tim R. Miles
*Assistant Examiner*—Gregory N. Clements
*Attorney, Agent, or Firm*—McGlew and Tuttle

[57] ABSTRACT

A vaporizer for anaesthetics or narcotics comprises a housing having an interior liquid anaesthetic reservoir and an evaporation chamber above the reservoir. An inlet into the housing divides so that there is a vaporizing flow passage over and through a coiled vaporizing tube wick in an annular passage down to the liquid anaesthetic, then upwardly in a central passage and past a regulatable annular passage to a discharge passage. The inlet also includes a bypass flow through a passage which joins an annular space above the vaporizing chamber portion above the anaesthetic liquid and back to the discharge passage. A control device is located in the second or bypass passage and comprises an annular trough-shape body having a closed bottom wall which is of a material of a high coefficient of thermal expansion. A hollow cylinder is positioned in the trough-shape annular body and forms a close fit therewith and has a low coefficient of thermal expansion relative to the trough-shape body. The hollow cylinder includes a top flange portion which is spaced below an annular ring member which is suspended from the housing by sealing means which includes an anchor. The ring member is made of a material of low coefficient of thermal expansion relative to the housing and the hollow cylinder and the trough-shape annular body. The annular ring member is spaced above the flange portion of the hollow cylinder and defines an annular gap therebetween.

7 Claims, 1 Drawing Figure

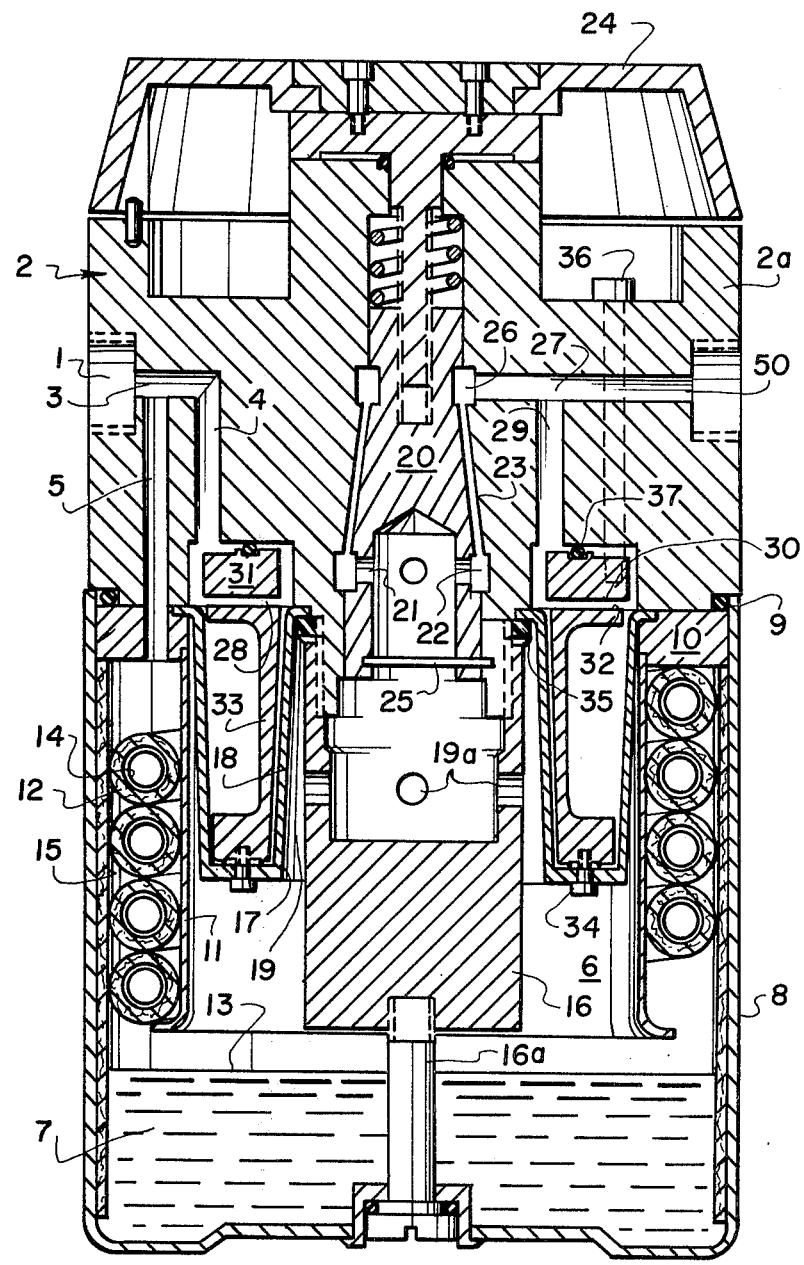

VAPORIZER FOR ANAESTHETICS

FIELD AND BACKGROUND OF THE INVENTION

This invention relates in general to the construction of a liquid evaporator and, in particular, to a new and useful evaporator for anaesthetics or narcotics, which includes a housing having an evaporation passage and a bypass passage which join at the outlet.

DESCRIPTION OF THE PRIOR ART

In the evaporation of narcotics or anaesthetics, the gas stream directed therethrough is enriched with a narcotic contained in the evaporator to a desired concentration. The gas stream directed through the evaporator of narcotics is divided into two partial streams, namely, a bypass stream and a main evaporation chamber stream. Both partial streams are controlled in an exact flow ratio to each other by means of valves of which at least one is adjustable for varying the concentration ratio. The evaporation chamber steam is conveyed through an evaporation chamber in which a supply of liquid narcotic is provided so that the stream becomes enriched with the narcotic in accordance with the vapor pressure which depends on temperature. The air stream which has been enriched with the narcotic is again reunited with the bypass stream at the discharge from the housing. The bypass portion flows through the housing without becoming changed in gas composition until it joins the other stream. The volumes of the two streams are controlled so as to provide a ratio to result in a desired gas mixture which has the desired concentration of narcotic. Since the vapor pressure depends on the temperature of the liquid narcotic, the concentration depends on the temperature also. Known evaporators of narcotics include devices for temperature compensation in order to attempt to eliminate the effect of temperature on the resultant content of the narcotic in the air stream which leaves the device. Such devices must also compensate for the cooling effect produced by the evaporation of the narcotic during the passage of the gas thereover. A known evaporator of narcotics includes an adjustable control valve which is mounted in the conduit leading through the evaporator in which the narcotic is evaporated, and also an adjustable bypass valve is mounted in the bypass extending parallel to the evaporator passage. Adjusting means are provided for each of these valves and the control valve and the bypass valve are mounted concentrically of each other. The valves include conical valve seats which are firmly connected to the housing. The movable bodies of the two valves are connected to each other through a temperature sensor which is provided in the evaporator. The adjustment of the concentration of the gas mixture is effected by the outside valve which is disposed concentrically about the inner central valve. Through the temperature sensor and as a function of the temperature of the narcotic, the central valve prevents variations of concentration which would be caused by variations of temperature. For this purpose, the temperature sensor adjusts the inner, movable, valve body. A difficulty of this construction is that the central valve adjusted by the temperature sensor has only a small diameter because of its position so that long adjusting paths are necessary to obtain a satisfactory variation of the cross-sectional area of the passage. Such adjusting paths with the temperature sensor are very difficult to design. The temperature sensor comprising a bellows filled with liquid effects the control through the temperature-responsive expansion of the liquid. A leakage of the bellows, which cannot be excluded, changes or prevents the function of the sensor and it may change the concentration of the narcotic in an uncontrollable and, therefore, dangerous manner.

Another evaporator of narcotics comprises a valve for controlling the concentration which is mounted in the conduit leading from the inlet through the evaporation chamber to the outlet. The valve is provided between the evaporation chamber and the outlet and is equipped with devices for the temperature compensation. At the near end of a second conduit, which serves as a bypass, there is an adjustable bypass valve. This adjustable bypass valve has a conical seat and a conical, movable valve body. In the interior of the movable valve body, and concentrically thereof, there is a spring-loaded excess pressure valve. Upon exceeding the adjusted limit pressure of the respiratory gas, the excess pressure valve opens and clears an additional cross-sectional area in the bypass stream. The valve controlling the concentration and the bypass valve are mounted adjacent each other. The valve seat of the valve for controlling the concentration is made of a stainless steel and, therefore, has a small coefficient of thermal expansion, while the movable valve body is made of a plastic and has a high coefficient of thermal expansion. The valve seat and the movable valve body are conical in shape. With the valve for controlling the concentration open, the passage opening has the form of a conical jacket. For the actuation, a handwheel is provided. Because of the unequal thermal expansion of the materials of the valve seat and the movable valve body, aside from the normal adjustment by means of the handwheel, an additional change of the passage opening is obtained which is dependent on the temperature of the evaporation chamber stream and which already provides for a partial compensation of the temperature influence. A complete temperature compensation is obtained with a further compensation device which is provided in the evaporation chamber stream, downstream of the valve controlling the concentration. This compensation device comprises an annular gap which is formed by component parts having unequal coefficients of thermal expansion in dependence on the temperature of the evaporation chamber stream and as in the case of the valve for controlling the concentration, is made of a stainless steel and plastic. The expansion of the plastics, due to the temperature, is non-linear which at certain temperatures leads to an over- or an under-compensation. In addition, in the presence of conventional narcotics, plastics tend to swell and this effect uncontrollably interferes with the temperature compensation. In addition, it must be taken into account that, upon pressure load, plastics tend to flow, so that the adjustment is further changed. A device of this nature is described in U.S. Pat. No. 3,420,232.

Another evaporator of narcotics comprises an evaporator-chamber conduit and a bypass provided with a control valve in each conduit, and these control valves have conical seats and conical mobile valve bodies. The two control valves are disposed adjacent each other and are coupled at each other in a manner such that, upon adjusting one of the control valves to an open position, the other valve is adjusted to a closed position. The control valve in the bypass performs two functions, namely, the control of the bypass stream and a compensation for the changed volume due to the temperature variation following the evaporation, and for the concentration of the evaporation-chamber stream. Both functions are fulfilled by a valve of varying cross-section. The variation of the valve cross-section may be effected both by an adjustment of the valve stem manually or by the thermal expansion of a sensing device. The sensing device comprises the valve stem extended to the evaporator chamber and which is surrounded by a sleeve connected thereto in the evaporation chamber. At its upper end remote from the concentration zone with the valve stem, the sleeve terminates in a conical valve body. The respective associated valve seat is located at the same level and forms a part of the bypass. The valve stem and the sleeve are made of materials having unequal coefficients of thermal expansion. Temperature differences in the evaporation chamber cause length variations both of the stem and the sleeve. These variations have an effect on the open cross-sectional area of the control valve in the bypass. Thus, the bypass is varied both by a turning of the valve stem and by temperature influences. By selecting materials for the stem and the sleeve, a temperature compensation is obtained. Because of the necessary gastight and movable extension of the sleeve through the wall of the evaporation chamber, this evaporator of narcotics is considerably expensive. Further, the influence of the temperature compensation on the passage opening of this valve varies depending on the respective adjustment of the bypass control valve. Finally, because of the conical annular gap, the necessary adjusting paths can be obtained from the unequal thermal expansion only with large overall lengths of the stem extension.

SUMMARY OF THE INVENTION

The present invention provides an evaporator for narcotics or anaesthetics having devices for preventing a temperature influence on the gas mixture composition, in which the temperature influence is compensated by a control device in the bypass even with rapidly varying supplies. This requires short adjusting paths. The construction actuation and maintenance are simple to effectuate and the device is reliable in operation under any conditions.

In accordance with the invention, the control device for the bypass is mounted concentrically about the control device for the evaporation chamber stream and it comprises a unilaterally closed hollow annular body of a material having a high coefficient of thermal expansion. A hollow cylinder is inserted into the hollow annular body which is closed on one side so as to tightly fit at the location of the connection therewith and it has a low coefficient of thermal expansion relative to the closed hollow annular body. The hollow cylinder has an end flange which is spaced from an annular body or ring member which is suspended from the housing through a seal construction and by means of anchors which are made of a material having a low coefficient of thermal expansion which is lower than that of the material of the housing. The surfaces of the ring member and the flange of the cylinder are spaced apart and form an annular gap therebetween. This large annular surface gap between these two members provides a passage area for the bypass gas which can be varied with short strokes of the control device in an axial direction. Because the two surfaces define a rectangular cross-section therebetween, the strokes of the two parts in directions toward or away from each other induce an effect directly on the cross-sectional flow area and not, as in conical annular gaps, through an angular function. In addition, these necessary short strokes are very advantageously obtained rapidly due to the double adjusting paths present in the compensation because the height of the annular gap varies by movement of the two surfaces which define the same.

In a development of the invention, the surface of the hollow cylinder is designed as a plane flange and the surface of the annular body or ring member is designed so that its opposing surface forms a plane perpendicular to the axis. Due to this advantageous design of the annular gap which is variable in height, a simple passage section is produced in the control device for the bypass which is directly variable.

By providing anchors as screw bolts, and by using an elastic sealing between the housing and the annular body, it is possible to vary the height of the gap for adjusting the bypass stream in a simple manner. The annular body is adjusted in its height by a simple turning of the screw connecting part to vary the position of the annular body relative to the flange of the cylinder. The elastic sealing permits a longer travel of the annular body.

In a further development of the evaporator for narcotics, a gas conveying body is provided within the space formed by the wall of the hollow annular body forming a passage gap along with the wall. This results in an advantageous conveying of the evaporation chamber stream alongside the compensation part formed with the hollow annular body so that temperature variations produce their effect directly and rapidly.

Accordingly, it is an object of the invention to provide a vaporizer for anaesthetics or narcotics which includes a housing having an inlet with a first vaporization flow path defined from the inlet through an annular chamber and over a reservoir in the housing for the narcotics and then upwardly to a discharge on the other side of the housing and which also includes a bypass conduit which extends in an annular passage in the housing and joins the discharge on the opposite side and which includes a trough-shape member closing the annular passage on the side adjacent the reservoir with a hollow cylinder fitted into the trough-shape member and having a planar surface opposed to a planar surface of a ring member which is adjustably suspended in the housing and which may be moved relatively to the ring member for varying the spacing therebetween and wherein the ring member is suspended by anchors which are made of a material of a low thermal coefficient of expansion, lower than that of the housing, so that the ring member is movably suspended over the cylindrical member.

A further object of the invention is to provide an evaporator device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there is illustrated a preferred embodiment of the invention.

BRIEF DESCRIPTION OF THE DRAWING

The only FIGURE of the drawing is a cross-sectional view of an evaporator constructed in accordance with the invention.

DESCRIPTION OF THE PREFERRED EMBODIMENT

Referring to the drawing in particular, the invention embodied therein, comprises a vaporizer for narcotics or anaesthetics which includes a housing, generally designated 2, having an inlet 1 on one side which includes an inlet passage 3 which communicates with a bypass conduit 4 and an evaporation chamber conduit 5. The incoming gas which flows through evaporation chamber conduit 5 passes downwardly over a spirally wound wick tube 12 and through the interior of the tube into an evaporation chamber 6 which is located over a liquid reservoir 7 for the narcotic or anaesthetic. The reservoir chamber is formed by a pot portion 8 of the housing which is connected through an annular seal 9 to the upper portion 2a in a gas-tight sealed manner. Seal 9 is retained by a ring 10, and on the inside, the ring carries a cylinder jacket 11 which is spaced inwardly from the interior wall or jacket 15 of the housing. The length of the cylinder jacket 11 is such that gas can exit from the wick tube 12 above the surface 13 of liquid 7. The evaporation chamber stream through the conduit 5 passes both on the interior and the exterior of the spirally wound wick tube 12 and tube 12 is supported on its inside by a spiral spring 14. Wick tube 12 is connected to the wick jacket 15 which is immeged into the narcotic 7 so that the liquid of the reservoir 7 rises along the wick tube through a capillary effect.

In accordance with a further feature of the invention, evaporator chamber 6 is provided with a gas-conveying body 16 which is supported above the liquid on a bolt 16a which is in threaded engagement therewith. The conveying body 16 is centered in the evaporation chamber 6 in respect to inner walls of an annular hollow body or trough-shape member 18. The gas passes through the passage 19 and through bores 19a of the body 16 and then through bores 21 of a dosing cone 20 and into an annular channel 22. A conical annular gap 23 is formed between dosing cone 20 and the housing upper portion 2a. A housing cover forms a handwheel 24 which is adjustable to shift the dosing cone 20 either upwardly or downwardly to vary the flow area in a ring gap 23 between the cone 20 and the housing 2a. A pin 25 prevents the turning of dosing cone 22 during the turning of handwheel 24. The evaporation chamber stream flows through the cone ring gap 23 into the annular channel 26 and reunites with the bypass stream at a junction 27 of a discharge passage 50.

The bypass stream flows through the bypass conduit 4 to the annular gap 28 which, in accordance with the invention, is defined between a flange portion of a hollow cylinder member 33 and the bottom of an annular body or ring member 31. The stream then flows through the bore 29 to the junction 27 where it unites with the evaporation conduit gases in the discharge 50.

In accordance with a feature of the invention, the annular gap 28 which is formed by the top or planar surface 32 of the hollow cylinder member 33 and the bottom or planar surface 30 of the ring member 31, defines an adjustable flow space for the bypass gas. The hollow cylinder 33 has a lower coefficient of thermal expansion than the trough-shape member or annular body 18. Both parts are tightly connected together by screws 34. The hollow annular body 18 is retained at its outside by the ring 10 and at its inside by a threaded ring 35. At temperature variations in the evaporation chamber, the different coefficients of thermal expansion between hollow body 18 and the hollow cylinder 33 effect a travel of the planar surface 32 whereby, the height of the annular gap 28 is changed. Annular body 31 is held by a sealing 37 on housing 2 by means of one or more screw bolts 36. Screw bolts 36 are made of a material having a smaller coefficient of thermal expansion than the housing 2a so that, due to the unequal expansion as a function of the temperature in the evaporation chamber stream, the height of the annular gap 28 will vary. In addition, by adjusting screw bolts 36 for adjusting the height of the annular gap 28 and, thereby, the free cross-section, the flow space can be varied.

While a specific embodiment of the invention has been shown and described in detail to illustrate the application of the principles of the invention, it will be understood that the invention may be embodied otherwise without departing from such principles.

What is claimed is:

1. A vaporizer for anaesthetics or narcotics comprising a housing having an interior liquid narcotic reservoir and an evaporation chamber above said reservoir, an inlet into said housing, an outlet passage in said housing spaced from said inlet, a first conduit for evaporation gases extending from said inlet to said evaporation chamber and from said evaporation chamber to said outlet passage, a second bypass conduit extending from said inlet to said outlet passage and having an annular portion, flow control means in said second bypass passage comprising an annular trough-shape member having a bottom wall closing one end of said annular portion, a hollow cylindrical member positioned in said trough-shape member and having a top planar wall, a ring-shape member having a bottom planar wall opposed to said top planar wall of said hollow cylindrical member, and sealing means including an anchor for suspending said annular ring member in said housing and being of a different thermal coefficient of expansion than said housing to permit relative movement of said ring member to vary the gap between said flat bottom surface of said ring member and said planar surface of said hollow cylinder member.

2. A vaporizer for anaesthetics or narcotics, according to claim 1, wherein said hollow trough-shape member comprises a material of a high thermal coefficient of expansion relative to said hollow cylinder, means connecting the cylinder to said trough-shape member.

3. A vaporizer for anaesthetics or narcotics, according to claim 1, wherein said hollow cylinder includes a flange portion defining said planar surface.

4. A vaporizer for anaesthetics or narcotics, according to claim 3, wherein said ring member bottom defines an annular planar surface disposed at right angles to the axis of said housing.

5. A vaporizer for anaesthetics or narcotics, according to claim 1, wherein said sealing means anchor comprises a screw bolt connected to said housing and to said ring member.

6. A vaporizer for anaesthetics or narcotics, according to claim 5, wherein said sealing means includes an elastic body disposed between said ring member and said housing.

7. A vaporizer for anaesthetics or narcotics, according to claim 1, including a conveying body centered over said reservoir, said annular trough-shape member being spaced from said conveying body and defining a flow passage gap therebetween, said first conduit including a vaporizing gas passage through said conveying body to said outlet passage, said housing having a conical portion in said evaporation gas passage, a cone positioned in said conical portion, and a handwheel connected to said cone for raising and lowering it in said conical portion for varying the cross-sectional flow therethrough to said outlet.

* * * * *